US00PP25250P2

(12) United States Plant Patent
Kako

(10) Patent No.: US PP25,250 P2
(45) Date of Patent: Jan. 27, 2015

(54) ***CATHARANTHUS* PLANT NAMED 'SUNNICHI TAHOME'**

(50) Latin Name: *Catharanthus roseus*
Varietal Denomination: Sunnichi Tahome

(71) Applicant: Tetsuya Kako, Shimane (JP)

(72) Inventor: Tetsuya Kako, Shimane (JP)

(73) Assignee: Suntory Flowers Ltd., Tokyo (JP)

( * ) Notice: Subject to any disclaimer, the term of this patent is extended or adjusted under 35 U.S.C. 154(b) by 18 days.

(21) Appl. No.: 13/986,653

(22) Filed: May 21, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — C. A. Whealy

(57) ABSTRACT

A new and distinct cultivar of *Catharanthus* plant named 'Sunnichi Tahome', characterized by its upright to outwardly spreading plant habit; vigorous growth habit; freely basal branching habit; freely flowering habit; long flowering period; relatively large white-colored flowers with red purple-colored centers; and good garden performance.

1 Drawing Sheet

Botanical designation: *Catharanthus roseus.*
Cultivar denomination: 'SUNNICHI TAHOME'.

BACKGROUND OF THE INVENTION

The present invention relates to a new and distinct *Catharanthus* plant, botanically known as *Catharanthus roseus* and hereinafter referred to by the name 'Sunnichi Tahome'.

The new *Catharanthus* plant is a product of a planned breeding program conducted by the Inventor in Higashiomi, Shiga, Japan. The objective of the breeding program is to develop new freely branching and vigorous *Catharanthus* plants with upright to outwardly spreading plant habit and numerous attractive flowers.

The new *Catharanthus* plant originated from a cross-pollination conducted by the Inventor in Higashiomi, Shiga, Japan in June, 2006 of a proprietary selection of *Catharanthus roseus* identified as code number Casp2-1, not patented, as the female, or seed, parent with a proprietary selection of *Catharanthus roseus* identified as code number Cacv10-1, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in April, 2007.

Asexual reproduction of the new *Catharanthus* plant by vegetative cuttings in a controlled greenhouse environment in Higashiomi, Shiga, Japan since April, 2007, has shown that the unique features of this new *Catharanthus* plant are stable and reproduced true to type in successive generations.

SUMMARY OF THE INVENTION

Plants of the new *Catharanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunnichi Tahome'. These characteristics in combination distinguish 'Sunnichi Tahome' as a new and distinct *Catharanthus* plant:

1. Upright to outwardly spreading plant habit.
2. Vigorous growth habit.
3. Freely basal branching habit.
4. Freely flowering habit.
5. Long flowering period.
6. Relatively large white-colored flowers with red purple-colored centers.
7. Good garden performance.

Plants of the new *Catharanthus* can be compared to plants of the female parent selection. Plants of the new *Catharanthus* differ primarily from plants of the female parent selection in flower petal color as plants of the female parent selection have pink-colored flower petals.

Plants of the new *Catharanthus* can be compared to plants of the male parent selection. Plants of the new *Catharanthus* differ primarily from plants of the male parent selection in the following characteristics:

1. Plants of the new *Catharanthus* are more upright than and not as trailing as plants of the male parent selection.
2. Plants of the new *Catharanthus* and the male parent selection differ in flower color as plants of the male parent selection have rose pink-colored flowers.

Plants of the new *Catharanthus* can be compared to plants of the *Catharanthus roseus* 'Sunnichihoho', disclosed in U.S. Plant Pat. No. 20,541. In side-by-side comparisons conducted in Higashiomi, Shiga, Japan, plants of the new *Catharanthus* differed from plants of 'Sunnichihoho' in the following characteristics:

1. Plants of the new *Catharanthus* were more upright than and not as trailing as plants of 'Sunnichihoho'.
2. Plants of the new *Catharanthus* were larger than plants of 'Sunnichihoho'.
3. Leaves of plants of the new *Catharanthus* had shorter leaves with rounded apices whereas leaves of plants of 'Sunnichihoho' were longer and had acute apices.

4. Plants of the new *Catharanthus* and 'Sunnichihoho' differed slightly in flower color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Sunnichi Tahome' grown in a container.

The photograph at the bottom of the sheet comprises a close-up view of a typical flower of 'Sunnichi Tahome'.

DETAILED BOTANICAL DESCRIPTION

The aforementioned photographs and following observations, measurements and values describe plants grown during the autumn and winter in 15-cm containers in an outdoor nursery in Higashiomi, Shiga, Japan and under cultural practices typical of commercial production. During the production of the plants, day temperatures averaged 25° C. and night temperatures averaged 15° C. Plants were four and six months old when the description and photographs, respectively, were taken. In the following description, color references are made to The Royal Horticultural Society Colour Chart, 2007 Edition, except where general terms of ordinary dictionary significance are used.

Botanical classification: *Catharanthus roseus* 'Sunnichi Tahome'.

Parentage:

*Female, or seed, parent*.—Proprietary selection of *Catharanthus roseus* identified as code number Casp2-1, not patented.

*Male, or pollen, parent*.—Proprietary selection of *Catharanthus roseus* identified as code number Cacv10-1, not patented.

Propagation:

*Type*.—By vegetative cuttings.

*Time to initiate roots, summer*.—About two weeks at 30° C.

*Time to initiate roots, winter*.—About three weeks at 25° C.

*Time to produce a rooted young plant, summer*.—About five weeks at 30° C.

*Time to produce a rooted young plant, winter*.—About six weeks at 25° C.

*Root description*.—Fibrous; white in color.

*Rooting habit*.—Freely branching; medium density.

Plant description:

*Plant and growth habit*.—Upright and outwardly spreading plant habit; freely basal branching habit with about six basal branches developing per plant; vigorous growth habit.

*Plant height*.—About 22.8 cm.

*Plant diameter*.—About 38.5 cm.

Lateral branch description:

*Length*.—About 20 cm.

*Diameter*.—About 2.9 mm.

*Internode length*.—About 2 cm.

*Strength*.—Strong.

*Aspect*.—Upright to outwardly.

*Texture*.—Smooth, glabrous.

*Color*.—Close to 144C tinted with close to 64D.

Foliage description:

*Arrangement*.—Opposite, simple.

*Length*.—About 5.6 cm.

*Width*.—About 2 cm.

*Shape*.—Narrowly elliptic.

*Apex*.—Rounded.

*Base*.—Obtuse.

*Margin*.—Entire.

*Texture, upper and lower surfaces*.—Pubescent.

*Venation pattern*.—Pinnate; reticulate.

*Color*.—Developing leaves, upper surface: Close to 143A. Developing leaves, lower surface: Close to 143B. Fully expanded leaves, upper surface: Close to 137A; venation, close to 144B. Fully expanded leaves, lower surface: Close to 143A; venation, close to 144D.

*Petiole*.—Length: About 6.9 mm. Diameter: About 1.6 mm. Texture, upper and lower surfaces: Pubescent. Color, upper and lower surfaces: Close to 145C tinted with close to 64D.

Flower description:

*Flower arrangement and habit*.—Single salverform flowers arising from upper leaf axils; freely flowering habit with usually about 14 flowers developing per plant; flowers face upright or outwardly.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower diameter*.—About 5.1 cm.

*Flower length (depth)*.—About 3.3 cm.

*Flower throat diameter*.—About 1.4 cm.

*Tube length*.—About 2.8 cm.

*Tube diameter, at the base*.—About 1.5 mm.

*Flower buds*.—Length: About 1.6 cm. Diameter: About 4.1 mm. Shape: Cylindrical to narrowly ovoid. Color: Close to 145B and 2B.

*Corolla*.—Arrangement: Five petals in a single whorl fused at the base into a tube. Petal length from throat: About 2.6 cm. Petal width: About 1.7 cm. Petal shape: Obovate. Petal apex: Attenuate. Petal margin: Entire; slightly undulate. Petal texture, upper and lower surfaces: Smooth, glabrous; velvety. Throat texture: Smooth, glabrous. Tube texture: Pubescent. Color: Petal, when opening and fully opened, upper surface: Close to N155B; towards the throat, close to 67B. Petal, when opening and fully opened, lower surface: Close to N155D. Throat: Close to 145C. Tube: Close to 145C.

*Calyx*.—Arrangement: Star-shaped tubular calyx with five sepals fused towards the base. Sepal length: About 3.7 mm. Sepal width: About 0.8 mm. Sepal shape: Lanceolate to narrowly deltoid. Sepal apex: Acute. Sepal margin: Entire. Sepal texture, upper and lower surfaces: Smooth, glabrous. Color, immature and mature, upper surface: Close to 143A. Color, immature and mature, lower surface: Close to 143A.

*Peduncles*.—Length: About 5.3 mm. Diameter: About 1.5 mm. Angle: Upright to outwardly. Strength: Strong. Texture: Smooth, glabrous. Color: Close to 144C.

*Reproductive organs*.—Stamens: Quantity per flower: Five. Stamen length: About 2.9 mm. Anther shape: Ellipsoidal. Anther size: About 1 mm by 2.8 mm. Anther color: Close to 150B. Pollen amount: Moderate. Pollen color: Close to 2C. Pistils: Quantity per flower: One. Pistil length: About 2.2 cm. Style color: Close to 145D. Stigma shape: Narrowly ellipsoidal. Stigma color: Close to N144D. Ovary color: Close to 144C. Seeds and fruits: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Sunnichi Tahome' as illustrated and described.

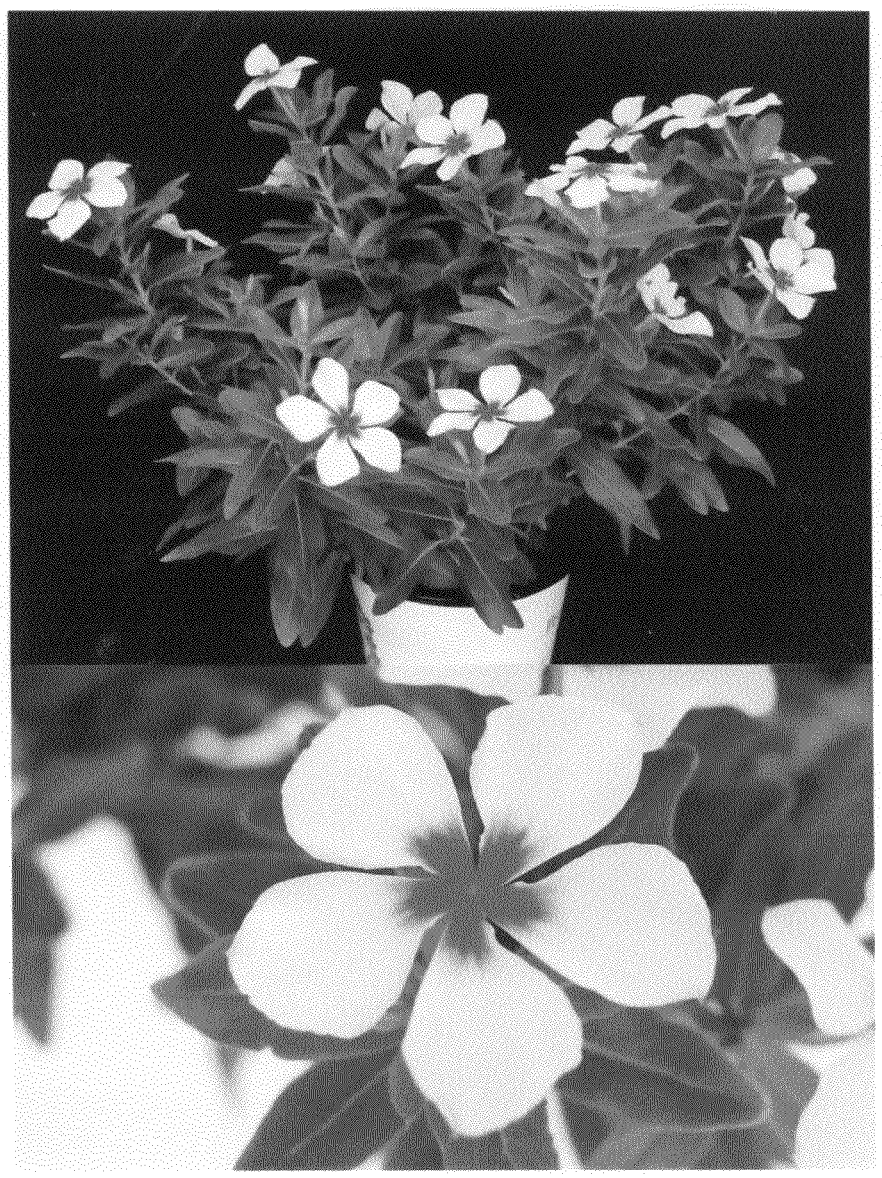

* * * * *